US00PP24795P3

(12) United States Plant Patent
Scheffers

(10) Patent No.: US PP24,795 P3
(45) Date of Patent: Aug. 19, 2014

(54) ***DRACAENA* PLANT NAMED 'DRAGONGDOR'**

(50) Latin Name: *Dracaena fragrans*
Varietal Denomination: Dragongdor

(75) Inventor: Ruud Scheffers, Honselersdijk (NL)

(73) Assignee: Dragon Tree Beheer B.V. (NL)

( * ) Notice: Subject to any disclaimer, the term of this patent is extended or adjusted under 35 U.S.C. 154(b) by 137 days.

(21) Appl. No.: 13/506,405

(22) Filed: Apr. 16, 2012

(65) Prior Publication Data

US 2013/0276195 P1 Oct. 17, 2013

(51) Int. Cl.
*A01H 5/00* (2006.01)

(52) U.S. Cl.
USPC ..... Plt./383

(58) Field of Classification Search
CPC ..... A01H 5/12; A01H 5/02
USPC ..... Plt./383
See application file for complete search history.

(56) References Cited

PUBLICATIONS

Jordi. Cuban buttercup on edge of hardiness zone here. News Leader story created Aug. 23, 2010, retrieved on Oct. 24, 2013. Retrieved from the Internet at <http://fbnewsleader.com/articles/2010/08/23/leisure/00aylbeckyjordi.txt> 2 pages.*

Spalding Bulb. *Dracaena* 'Dorado' Plant 2013, retrieved on Oct. 30, 2013. Retrieved from the Internet at <http://www.spaldingbulb.co.uk/product/dracaena-dorado-/> 2 pages.*

Variety Central: Foliage and Tropicals Dec. 6, 2009, retrieved on Oct. 24, 2013. Retrieved from the Internet at <http://www.todaysgardencenter.com/varieties/houseplants-tropical/variety-central-foliage-and-tropicals/> 3 pages.*

* cited by examiner

*Primary Examiner* — June Hwu
(74) *Attorney, Agent, or Firm* — Cassandra Bright

(57) ABSTRACT

A new and distinct *Dracaena* cultivar named 'Dragongdor' is disclosed, characterized by wide green leaves with yellow margins. The new variety is a *Dracaena*, typically produced as an ornamental plant.

1 Drawing Sheet

Latin name of the genus and species: *Dracaena fragrans*.
Variety denomination: 'Dragongdor'.

BACKGROUND OF THE INVENTION

The new cultivar is the product of chance discovery. The new variety originated as a naturally occurring branch mutation of the variety of *Dracaena fragrans* '004027J', U.S. Plant Pat. No. 21,830.

The new variety was discovered by the inventor, Ruud A. M. Scheffers, a citizen of the Netherlands, in July of 2009 in a commercial greenhouse belonging to the inventor in Honselersdijk, The Netherlands. After identifying the new variety as a potentially interesting selection, the inventor continued confidential testing and propagation of 'Dragongdor' assessing stability of the unique characteristics of this variety.

Asexual reproduction of the new cultivar 'Dragongdor' was first performed at the commercial greenhouse of the inventor in Honselersdijk, The Netherlands by vegetative cuttings in July of 2009. Access to all plants was restricted, as plants were kept in a locked greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'Dragongdor' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Dragongdor'. These characteristics in combination distinguish 'Dragongdor' as a new and distinct *Dracaena* cultivar:

1. Wide green leaves with yellow margins.

PARENT COMPARISON

Plants of the new cultivar 'Dragongdor' are similar to the parent, *Dracaena fragrans* '004027J' U.S. Plant Pat. No. 21,830 in most horticultural characteristics. The new variety, however, produces leaves with a different color of margin compared to those of the parent.

COMMERCIAL COMPARISON

'Dragongdor' is in plant habit, and other horticultural characteristics most similar to the parent variety. 'Dragongdor' can however be compared to the commercial variety *Dracaena fragrans* 'Lauren', U.S. Plant Pat. No. 21,549. Plants are of the same species and both with variegated foliage. However, plants of 'Dragongdor' have distinctively twisted foliage, thicker foliage and a variegation pattern with a dark green leaf and creamy yellow margin. Plants of 'Lauren' produce green foliage with green-white streaks.

BRIEF DESCRIPTION OF THE PHOTOGRAPH

The accompanying photograph in FIG. 1 illustrates in full color a typical plant of 'Dragongdor' grown in a commercial greenhouse in Honselersdijk, The Netherlands. This plant is approximately 2 months old, shown planted in a 15 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'Dragongdor' plants grown in a greenhouse in Honselersdijk, The Netherlands. A steady temperature of approximately 20° C. at night and 20° C. during the day was maintained. No artificial light, photoperiodic treatments were given to the plants. Measurements and numerical values represent averages of typical plant types.

Botanical classification: *Dracaena fragrans* 'Dragongdor'.

PROPAGATION

Time to initiate rooting: About 4 weeks at approximately 20° C. 6 weeks for full rooting.

Root description: Moderately thick, moderately fibrous, not fleshy, young roots Yellow-White 158D, older roots Greyed-Orange 163D.

PLANT

Age of plant described: 2 months.

Pot size of plant described: 15 cm pot.

Growth habit: Broad upright.

Height: Approximately 20.8 cm.

Plant spread: Approximately 49.5 cm.

Growth rate: Moderate, approximately 6 cm per month.

Branching characteristics: Not free branching, growing with one main stem from the base. Will only develop lateral branches after pinching/pruning.

Diameter of stem: Approximately 2.1 cm. Stem not visible but fully covered by leaves, individual stem characteristics outside of diameter are not measurable.

Internode length: Average 0.4 cm.

Texture of stem: Stem not visible but fully covered by leaves.

Color of stem: Stem not visible but fully covered by leaves.

Stem strength: Very strong.

Number of leaves per stem: Average 22.

FOLIAGE

Leaf:

*Arrangement*.—Alternate (spirally).

*Average length*.—Approximately 30.2 cm.

*Average width*.—Approximately 7.2 cm.

*Shape of blade*.—Lorate.

*Aspect*.—Average angle at base: 50°, tips curved downward in an average angle of −45° (0°=vertical).

*Apex*.—Acuminate, not sharp.

*Base*.—Broad cuneate.

*Attachment*.—Sheathing.

*Margin*.—Entire, undulate.

*Texture of top surface*.—Smooth, very glossy.

*Texture of bottom surface*.—Smooth, moderately glossy.

*Color*.—Young foliage upper side: Near RHS N137A but darker, margins (average width 2 mm) near Yellow-Green 154B. Young foliage under side: Near RHS Green 143C to Yellow-Green144A, margins (average width 2 mm) near Yellow-Green 154B. Mature foliage upper side: In between near RHS N137A and Yellow-Green 147A but darker, closest to N137A, margins (average width 6 mm) near 9C. Mature foliage under side: Near RHS 137B, margins (average width 6 mm) near Yellow 9C and Yellow 11A.

*Venation*.—Type: Parallel. Color: Upperside: As leaf blade. Underside: As leaf blade.

Sheath:

*Average length*.—Approximately 1.1 cm.

*Average width*.—Approximately 1.0 cm.

*Color*.—Near RHS Green-White 157D, margins near Yellow-Green 147D.

*Texture*.—Smooth, glossy.

OTHER CHARACTERISTICS

Flower production: Not observed.

Disease and pest resistance: Neither resistance nor susceptibility to normal diseases and pests of *Dracaena* has been observed.

Drought tolerance and temperature tolerance: Moderately high drought resistance, good heat resistance.

Fruit/seed production: Not observed.

What is claimed is:

1. A new and distinct cultivar of *Dracaena* plant named 'Dragongdor' as herein illustrated and described.

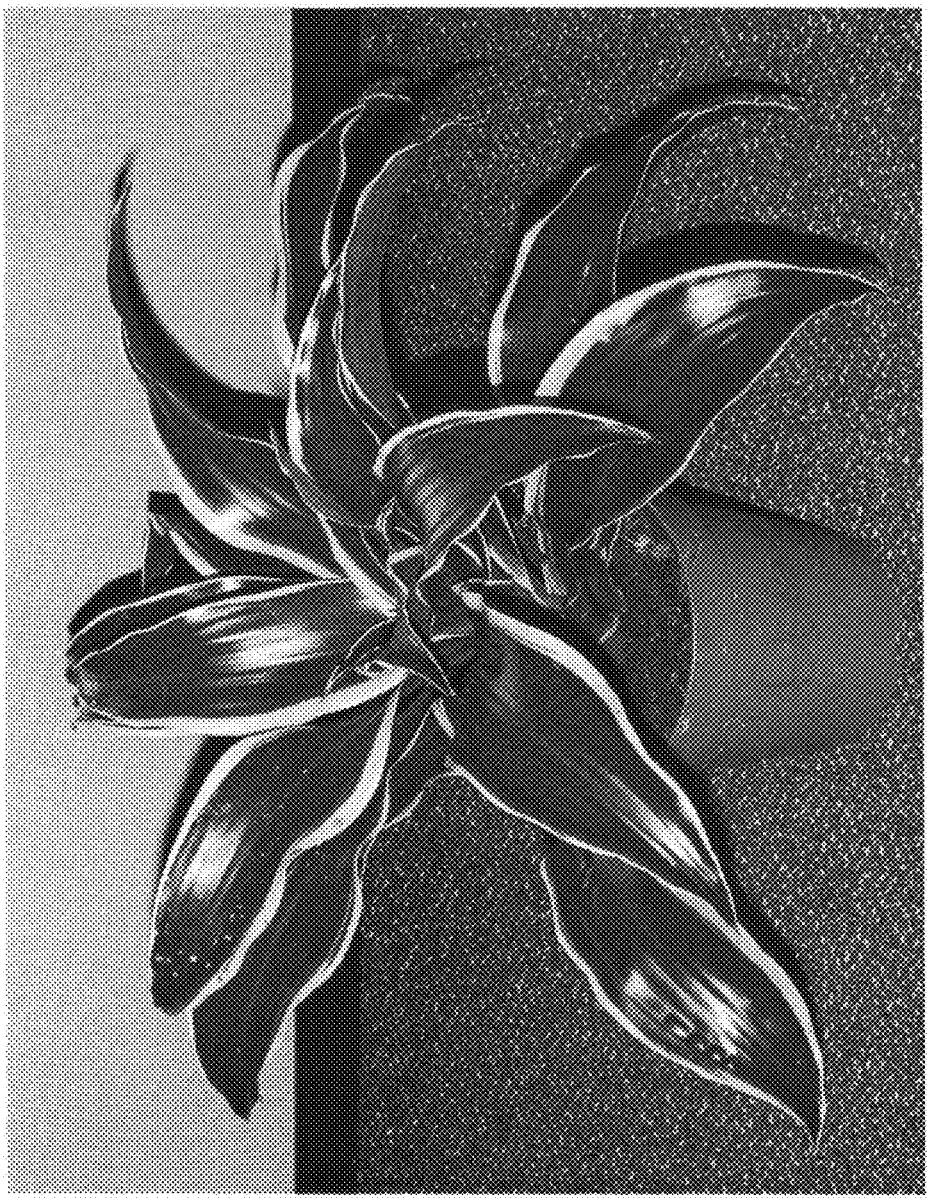

* * * * *